United States Patent
Danek et al.

(10) Patent No.: US 6,200,311 B1
(45) Date of Patent: Mar. 13, 2001

(54) MINIMALLY INVASIVE TMR DEVICE

(75) Inventors: Christopher J. Danek, Palo Alto; Miriam H. Taimisto, San Jose; Tyler Baughman, Campbell; Kevin Gertner, San Jose; John Valenti; Burt Uebelhoer, both of Morgan Hill, all of CA (US)

(73) Assignee: Eclipse Surgical Technologies, Inc., Sunnyvale, CA (US)

( * ) Notice: Subject to any disclaimer, the term of this patent is extended or adjusted under 35 U.S.C. 154(b) by 0 days.

(21) Appl. No.: 09/009,755

(22) Filed: Jan. 20, 1998

(51) Int. Cl.$^7$ ................................................ A61B 17/00
(52) U.S. Cl. ........................... 606/15; 606/19; 606/42; 606/1; 607/122
(58) Field of Search .................... 600/439, 461, 600/471; 606/19, 159, 1, 41–43, 169–171, 7, 14–15; 607/122, 116

(56) References Cited

U.S. PATENT DOCUMENTS

| | | | |
|---|---|---|---|
| 4,353,358 | 10/1982 | Emerson | 128/4 |
| 4,669,465 | 6/1987 | Moore et al. | 128/303.1 |
| 4,708,434 | 11/1987 | Tsuno | 350/96.26 |
| 4,714,075 | 12/1987 | Krauter et al. | 128/4 |
| 4,841,950 | 6/1989 | Fukuda | 128/4 |
| 4,846,171 | 7/1989 | Kauphusman et al. | 128/303.1 |
| 4,881,524 | 11/1989 | Boebel et al. | 128/6 |
| 4,924,852 | 5/1990 | Suzuki et al. | 128/4 |
| 4,986,257 | 1/1991 | Chikama | 128/4 |
| 5,168,864 | 12/1992 | Shockey | 128/4 |
| 5,243,679 | 9/1993 | Sharrow et al. | 385/135 |
| 5,275,151 | 1/1994 | Shockey et al. | 128/4 |
| 5,318,008 | 6/1994 | Bullard | 128/4 |
| 5,324,283 | 6/1994 | Heckele | 606/15 |
| 5,325,845 | 7/1994 | Adair | 128/4 |
| 5,327,906 | 7/1994 | Fideler | 128/772 |
| 5,331,948 | 7/1994 | Utsumi et al. | 128/4 |
| 5,342,299 | 8/1994 | Snoke et al. | 604/95 |
| 5,389,096 | 2/1995 | Aita et al. | 606/15 |
| 5,415,158 | 5/1995 | Barthel et al. | 128/4 |
| 5,423,804 | 6/1995 | Kulick | 606/14 |
| 5,454,787 | 10/1995 | Lundquist | 604/95 |
| 5,549,601 | 8/1996 | McIntyre et al. | 606/15 |
| 5,551,945 | 9/1996 | Yabe et al. | 600/122 |
| 5,607,421 | 3/1997 | Jeevanandam et al. | 606/15 |

(List continued on next page.)

FOREIGN PATENT DOCUMENTS

WO 97/13468  4/1997  (WO).
WO 97/15236  5/1997  (WO).

OTHER PUBLICATIONS

Eclipse Surgical Technologies, Inc. SoloGrip™ II, Single Use, fully disposable laser handpiece for Eclipse TMR, Copyright 1997.

*Primary Examiner*—Francis J. Jaworski
(74) *Attorney, Agent, or Firm*—Edward J. Lynch; William B. Anderson; Ilene Lapidus Janofsky

(57) ABSTRACT

The disclosure is directed to a tissue ablation device comprising an elongate probe, with a tissue ablation member located at the deflectable distal end of the probe, which is configured to access a patient's heart. The elongate probe is attached at its proximal end to a handpiece which is ergonomically designed to fit within the hand of the operator. The handpiece houses an advancement mechanism which is mechanically coupled to the tissue ablation member and can be used to axially translate the tissue ablation member in relation to the elongate probe. An activation mechanism is housed within the advancement mechanism and is coupled to the advancement mechanism in such a manner that the operator can simultaneously activate and advance the tissue removal member with one finger or thumb. The handpiece also houses a deflection actuator which applies tension to a tensile member which deflects the distal end of the probe.

34 Claims, 13 Drawing Sheets

U.S. PATENT DOCUMENTS

| | | | |
|---|---|---|---|
| 5,685,857 | 11/1997 | Negus et al. | 604/170 |
| 5,713,894 | 2/1998 | Murphy-Chutorian et al. | 606/15 |
| 5,738,680 | 4/1998 | Mueller et al. | 606/15 |
| 5,807,383 * | 9/1998 | Kolesa et al. | 606/7 |
| 5,807,388 | 9/1998 | Jeevanandam et al. | 606/15 |
| 5,871,495 | 2/1999 | Mueller | 606/185 |
| 5,876,373 | 3/1999 | Giba et al. | 604/95 |
| 5,913,853 | 6/1999 | Loeb et al. | 606/15 |
| 5,947,989 * | 9/1999 | Shikhman et al. | 606/180 |
| 5,976,121 * | 11/1999 | Matern et al. | 606/1 |
| 5,976,164 | 11/1999 | Bencini et al. | 606/170 |
| 5,980,545 * | 11/1999 | Pacala et al. | 606/170 |

\* cited by examiner

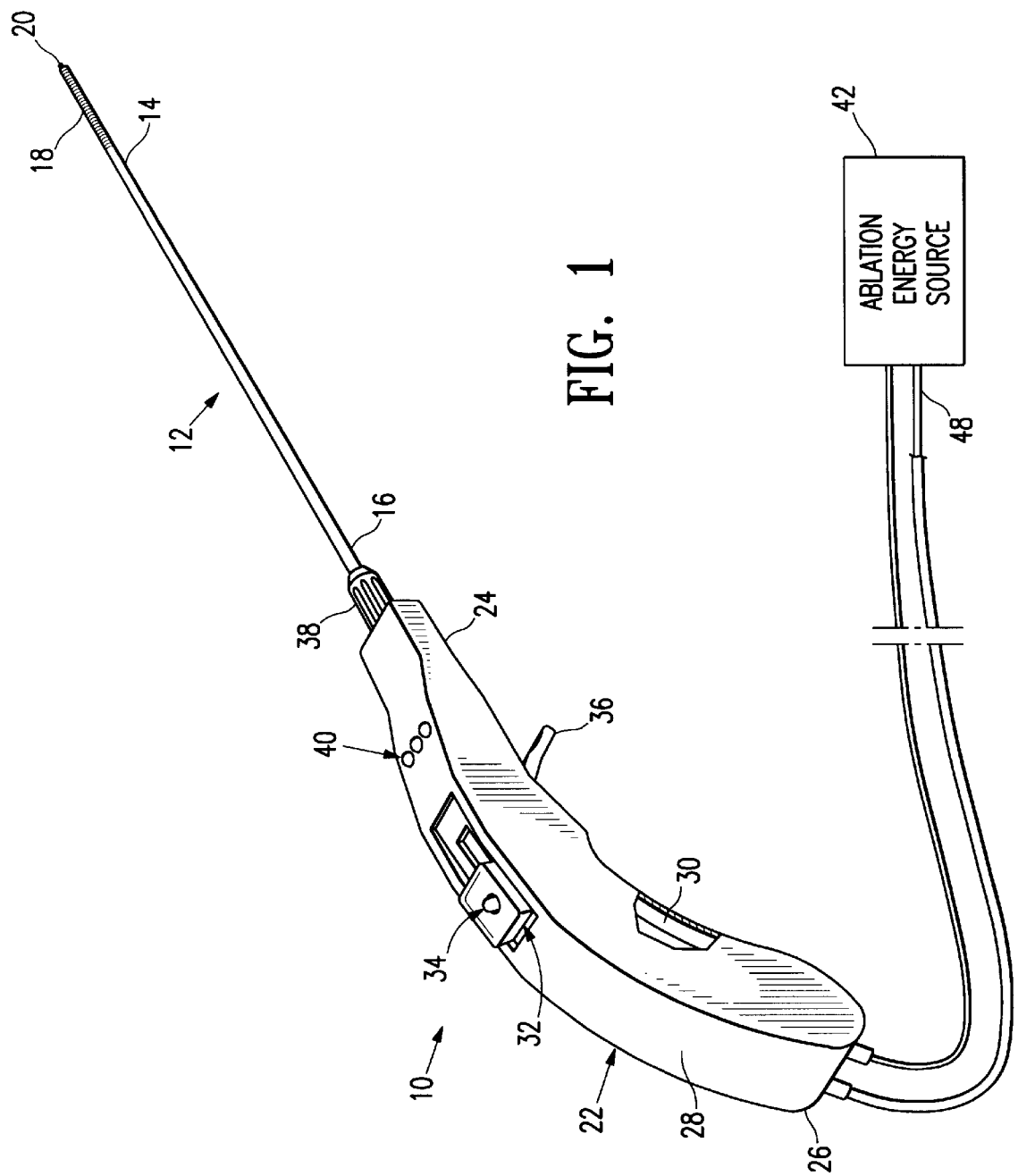

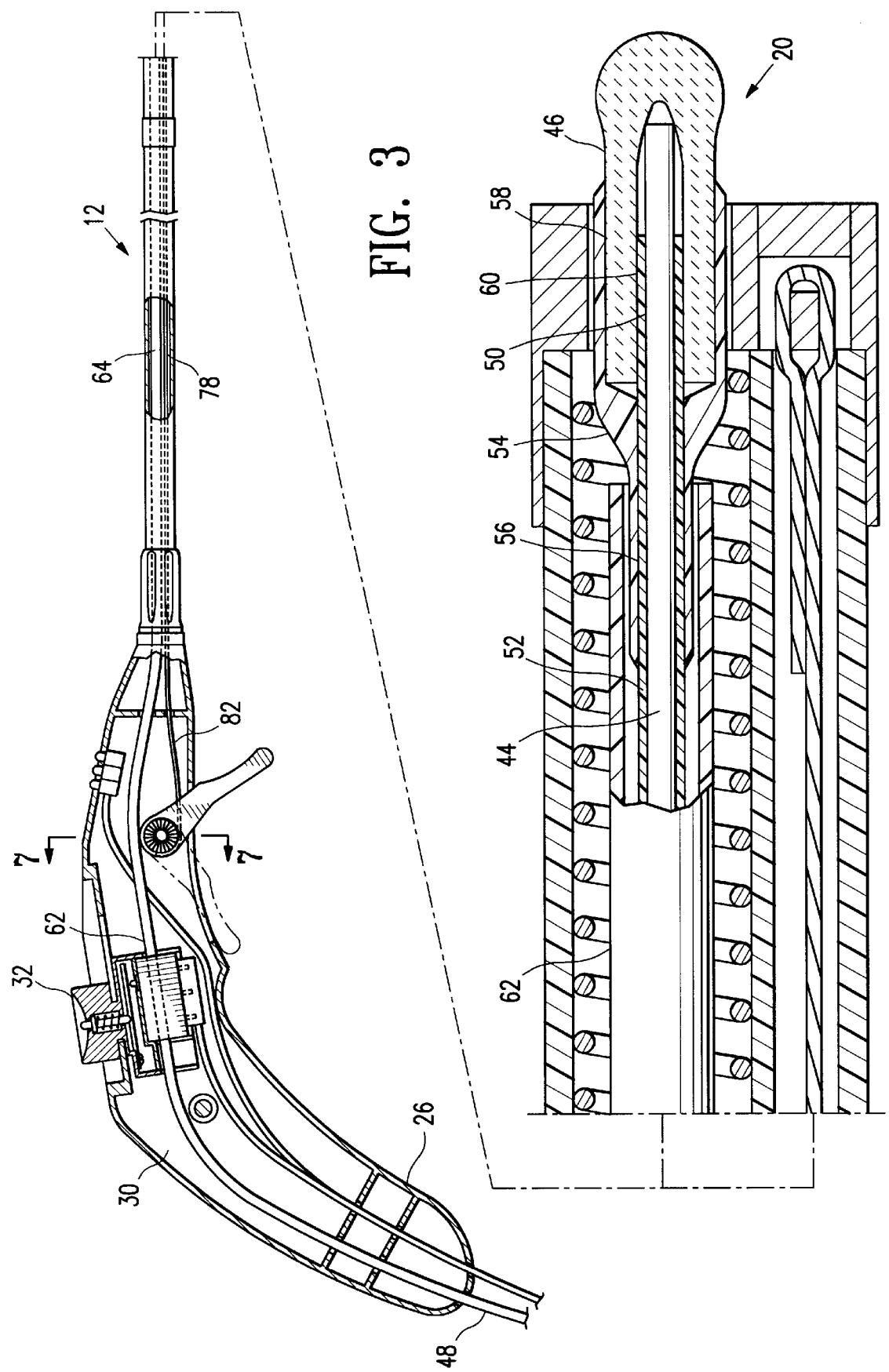

MINIMALLY INVASIVE TMR DEVICE

BACKGROUND

The number and variety of medical methods available to treat cardiovascular disease has increased rapidly in recent years. More particularly, alternatives to open heart surgery and cardiovascular by-pass surgery have been extensively investigated, resulting in less invasive procedures such as percutaneous transluminal coronary angioplasty, laser angioplasty, and atherectomy. These procedures are primarily directed toward the reduction of stenoses within the vasculature of a patient by either expanding the lumen through the use of a balloon, or otherwise removing the material making up the stenosis.

While these procedures have shown considerable promise, many patients still require by-pass surgery due to the presence of extremely diffuse stenotic lesions, the presence of total occlusions and the presence of stenotic lesions in extremely tortuous vessels. Also, some patients are too infirm to successfully undergo the rigors of by-pass surgery, and because the above treatments may require surgical intervention if complications develop, these patients are untreatable.

One alternative to these procedures is known as trans-myocardial revascularization (TMR). In TMR, channels are formed in the ventricle wall with a laser or other type of ablation device. These channels provide blood flow to ischemic heart muscle. A history and description of this method is presented by Dr. M. Mirhoseini and M. Cayton in "Lasers in Cardiothoracic Surgery" in *Lasers In General Surgery* (Williams and Wilkins; 1989 (pp. 216–223).

In the procedure described therein, after surgically opening the patient's chest to expose the heart, a carbon dioxide laser is used via an articulated arm delivery device to produce channels in the ventricle from the epicardium through to the myocardium. External pressure is used on the outside of the heart to stop bleeding from the ventricle through the newly created channel. Other early disclosures of this procedure are found in an article by Okada et al. in *Kobe J. Med. Sci.* 32, 151–161, October 1986 and U.S. Pat. No. 4,658,817 (Hardy). These early references describe intraoperative revascularization procedures which require an opening in the chest wall and include formation of the channels through the heart wall.

A proposed improvement in the design is described in Hardy—U.S. Pat. No. 4,658,817. A needle is added to the distal tip of the articulated arm system, with laser energy passing through the lumen of the needle. The metal tip of needle of the device is used to pierce the myocardium and the laser beam is used to create the desired channel through the remaining portion of the myocardium and through the adjacent endocardium. For a variety of reasons, the system of Hardy has not been used clinically to any significant extent. These prior procedures required the chest wall be opened in order to access the heart muscle with laser devices, which was highly invasive and resulted in severe complications.

A further improvement to the intraoperative TMR procedure is described in Aita—U.S. Pat. No. 5,554,152, issued Sep. 10, 1996, which is hereby incorporated by reference in its entirety wherein an elongated flexible lasing apparatus is inserted into the chest cavity of a patient and lasing channels are then formed in the heart wall. While the system of Aita has been found to be clinically quite successful, the system did not allow for easy access to the entire heart and was not always suitable for minimally invasive procedures through the chest wall.

What has been needed is a tissue ablation device with a probe that has the proper shape and configuration and sufficient maneuverability to access the desired areas of a patient's heart, particularly in minimally invasive procedures. The present invention satisfies these and other needs.

SUMMARY

The present invention is directed to an improved tissue ablation device which has an elongate probe with a proximal end and a distal end and which is configured to access desired regions of a patient's heart through port incisions, limited thoracotomy, or mini-sternotomy. The invention further comprises a handpiece which is attached to the proximal end of the elongate probe. The probe is rotatably attached to handpiece to allow rotation and manipulation within the patient's chest cavity while the handpiece held by the operator is outside the patient's chest. The handpiece may be ergonomically designed to fit within the hand of the operator to give the operator the grip and control on the elongate probe necessary to advance the probe through a small hole or trocar sheath in the patient's chest and reach the desired region of the patient's heart.

In one presently preferred embodiment, the handpiece is provided with an advancement mechanism which is mechanically coupled to the tissue ablation member at the distal end of the probe such that the advancement mechanism can be used to axially translate the tissue ablation member in relation to the elongate probe. The handpiece is also provided with an activation mechanism which is housed within the advancement mechanism and which controls activation of the tissue ablation member. In addition, the activation mechanism is coupled to the advancement mechanism in such a manner that the operator of the embodiment of the invention can simultaneously activate and advance the tissue ablation with one finger or thumb. This feature facilitates a coordination of movements and allows greater control over the manner in which tissue is removed from the patient's heart.

The embodiment of the activation mechanism also includes a cantilevered beam which is attached to the advancement mechanism and which is mechanically coupled to a button shaft. The free end of the beam is configured in a spaced relation to a plurality of electrical switches, such that depression of the button shaft translates the cantilevered beam so as to engage the electrical switches substantially simultaneously. The cantilevered beam is preferably configured to resist displacement as force is applied to it, until a threshold force is reached, at which point the cantilevered beam suddenly collapses with a resulting high acceleration of the free end of the cantilevered beam. The high acceleration of the beam upon collapse results in a high velocity at the time of engagement of the electrical switches, ensuring substantially simultaneous activation of the multiple electrical switches.

In a presently preferred embodiment, the invention includes an elongate probe which can be formed in a variety of shapes or curves, including, but not limited to, an "S" curve and a radiused curve, to facilitate access to various regions of a patient's heart. Improved access to the heart by the elongate probe can be further enhanced by the ability to change the shape of the elongate probe in vivo. Therefor, the distal section of the probe can further include a deflection mechanism which for a preferred embodiment has a flexible member with at least one lumen extending therethrough and a tensile member mechanically coupled to the distal end of the elongate probe offset from the longitudinal axis of the flexible distal end of the probe.

The handpiece further comprises a deflection actuator which includes means for pulling on the tensile member and thereby deflecting the distal end of the elongate probe. It may also be desirable for the operator of the device to fix the deflection of the distal end of the probe without the need to maintain force on the lever member. Therefor, the deflection actuator preferably includes a clutch which applies sufficient friction to the deflection actuator that it will maintain the deflected position of the distal end of the elongate probe unless force is applied to the deflection actuator by the operator of the device.

The deflection mechanism of the elongate probe may also include a resilience member disposed around the lumen or lumens of the flexible member such that kinking of the lumens of the distal end is prevented during deflection. The resilience member is preferably comprised of a helical coil of metal or other material that maintains longitudinal flexibility but resists collapse of the circular cross section during deflection of the distal end.

The handpiece of the preferred embodiment may also comprise an indicator disposed on the hand piece which typically embodies a plurality of lights or light-emitting diodes which, based on the illumination configuration, indicate the status of the tissue ablation member. The combination in the present embodiment of the invention of a handpiece, an elongate probe having various shape configurations and deflection capability of the distal end, and a tissue ablation member that can be both activated and advanced with one finger or thumb. This latter feature provides the user with a means for gripping the probe that provides for the requisite mechanical control of the probe to maneuver it within the chest cavity of a patient to any desired region of the patient's heart. Also provided is efficient coordination of the various functions necessary to perform the TMR procedure, such as activating and advancing the tissue ablation member, and deflecting the distal end of the probe within the chest cavity.

BRIEF DESCRIPTION

FIG. 1 shows a perspective view of the ablation device connected to a laser energy source.

FIG. 3 is an elevational view of the ablation device in partial section.

DETAILED DESCRIPTION

Figure 2A:
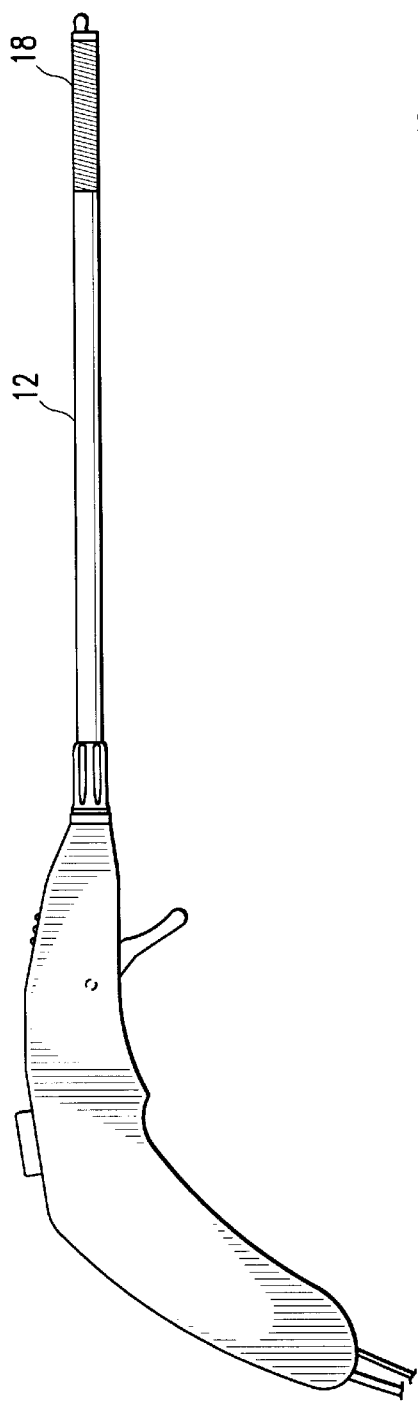
FIG. 2 is an elevational view of the device with an illustration of three versions of the elongate probe configurations.

FIG. 1 shows a tissue ablation device 10 having some of the features of the invention which includes an elongate probe 12, having a distal end 14, a proximal end 16, and a deflection mechanism 18 located at the distal end. A tissue ablation member 20 is disposed at the distal end of the elongate probe, configured to ablate tissue adjacent to the distal end of the elongate probe. The deflection mechanism 18 is disposed at the distal end of the elongate probe 14 so as to provide for deflection of the distal end of the elongate probe.

The tissue ablation device 10 further comprises a handpiece 22 having a distal end 24, a proximal end 26, and an outer wall 28 defining an interior cavity 30. An advancement mechanism 32, an activation mechanism 34, a deflection actuator 36, a rotator 38, and an indicator 40, are all operatively housed by the handpiece 22. The rotator 38 is rotatably housed on the distal end of handpiece 24, and configured to receive the proximal end of the elongate probe 16, which is attached thereto. Thus, by moving the rotator 38 at the distal end of the handpiece 24, the elongate probe 12 can be rotated about its longitudinal axis.

The advancement mechanism 32 is disposed upon the handpiece 22 in an operative configuration and is mechanically coupled to the tissue ablation member 20 at the distal end of the elongate probe 14, such that the tissue ablation member 20 can be axially translated by use of the advancement mechanism 32. Housed within the advancement mechanism 32 is a mechanism 34 which activates an ablation energy source 42. The advancement mechanism 32 and the activation mechanism 34 are coupled so as to enable the simultaneous operation of both mechanisms with a single finger or thumb.

The handpiece 22 may also include a deflection actuator 36 which operates the deflection mechanism 18 at the distal end of the elongate probe 14. In addition, the handpiece 22 has an indicator 40, which is disposed upon the outer wall 28 of the handpiece 22 in a viewable location, and which is electrically coupled to an ablation energy source 42, and which indicates the status of the ablation energy source.

Figure 2B:
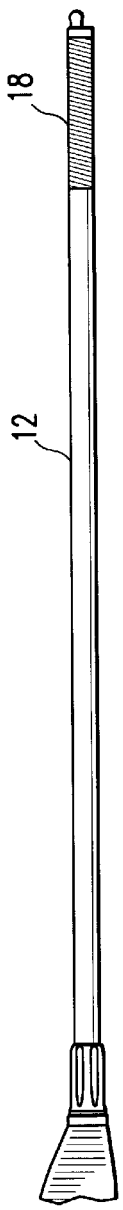
Figure 2C:
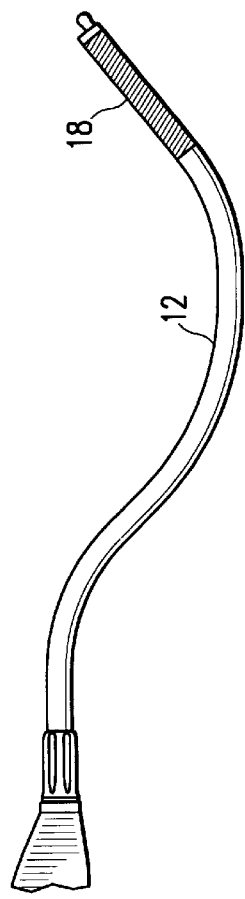

The elongate probe 12 can exist in a straight configuration, but preferably is shaped to provide the user with better access to the anatomy within a patient's chest cavity. The shapes, as depicted by FIGS. 2A, 2B, and 2C can include, but are not limited to, an "S" shape and a long or short straight shape. One of the preferred configurations for the elongate probe is a short straight version, which is shown in FIG. 2A, which has little or no bend, and is about 2 inches (5.08 cm) to about 6 inches (15.04 cm) in length, preferably about 3 inches (7.62 cm) to about 5 inches (12.7 cm) in length. Another preferred configuration of the elongate probe is the long straight probe, which is shown in FIG. 2B, and which is about 6 inches (15.04 cm) to about 10 inches (25.4 cm) in length, with little or no curvature. A further preferred configuration of the elongate probe is the short anatomically shaped probe, which about 4 inches (10.16 cm) to about 6 inches (15.04 cm) in length, configured in a "S" shape which is designed to enter through a patient's chest, and bend around the patient's heart without being obstructed by it, in order to access difficult to reach areas of the heart.

The elongate probe 12 is preferably comprised of a high strength bio-compatible material, such as stainless steel, a shape memory or psuedo-elastic NiTi alloy, MP35N alloy, carbon fiber composite or other suitable material. The outer diameter of the elongate probe 12 can be about 0.04 inches (1 mm) to about 0.24 inches (6 mm), preferably about 0.12 inches (3 mm) to about 0.20 inches (5 mm).

FIG. 3 depicts an embodiment of the invention where the tissue ablation member 20 is an optical fiber 44 terminating in a lens member 46. The optical fiber 44 has a proximal end 48, a distal end 50, and is coated with a protective coating 52. The lens member 46 is cylindrically shaped and comprised of a material that transmits laser energy, preferably quartz or silica. The lens member 46 is at least partially disposed within a sleeve 54 which is attached to the distal end of the optical fiber 50 by a mechanical crimp 56. The crimped sleeve 54 is bonded to the lens member 46 with an adhesive 58 which is preferably cyanoacrylate, but can be any suitable bonding agent such as an epoxy. In addition, the fiber optic coating 52 which is coated over the distal end of the fiber optic 50, terminates with a bond to lens member 46 with adhesive 60, which is preferably an ultraviolet radiation cured adhesive, but may be any type of suitable bonding agent such as an epoxy. The optical fiber 44 is generally coated with a protective coating 52 throughout its length, and is disposed within a protective sleeve 62 which is slidably disposed within an elongate probe lumen 64 of the elongate probe 12. Although the elongate probe 12 is shown having a single elongate probe lumen 64 extending longitudinally, it can also have multiple lumens extending in the longitudinal direction.

Proximal to the elongate probe, the fiber optic 44 and protective sleeve 62 are coupled to the advancement mechanism 32 within the interior cavity of the handpiece 30 such that advancing the advancement mechanism 32 translates the distal end of the fiber optic 50 and the lens member 46 in relation to the elongate probe 12. The optical fiber 44 exits the proximal end of the handpiece 26 and is thereafter energetically coupled at its proximal end 48 to an ablation energy source 42, or other tissue treatment source, as shown in FIG. 1.

The ablation energy source 42 is preferably comprised of a laser energy source such as HO:YAG, or Carbon Dioxide. However, any type of laser that produces ablative energy which can be transmitted through a flexible conduit could be used. The ablation energy source 42 can alternatively be comprised of a mechanical rotational energy source for powering a rotational mechanical tissue ablation member. It could also be an RF energy source, an ultrasonic energy source, or a high pressure fluid energy source. Note that any of the above mentioned energy sources could function as either continuous or pulsed energy sources, and could be used to perform TMR in ablation or non-ablation mode.

Figure 4:
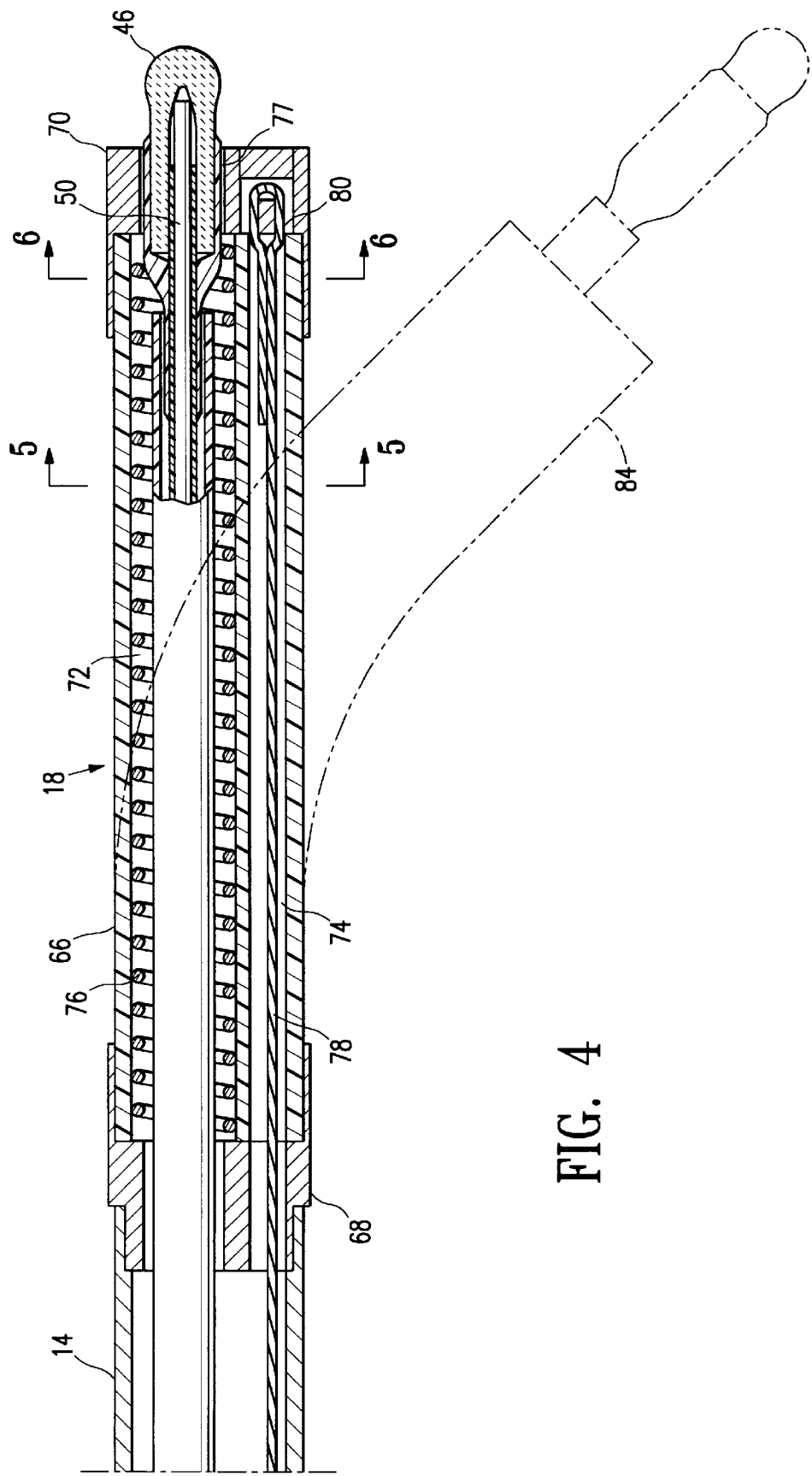
FIG. 4 is an elevational view of the distal end of the elongate probe, and a shadow view of the distal end in a deflected configuration with the tissue ablation member advanced distally.

Referring to FIG. 4, preferably, the distal end of the elongate probe 14 has a deflection mechanism 18 which is comprised of a flexible member 66, disposed between a proximal deflection cap 68 and a distal deflection cap 70.

The flexible member 66 has a tissue ablation member lumen 72 and a deflection mechanism lumen 74 disposed within and offset from the longitudinal axis of the deflection mechanism 18. The distal end of the optical fiber 50 and the protective sleeve 62 are partially disposed within the tissue ablation member lumen 72 of the flexible member 66. The deflection mechanism 18 preferably includes a resilience member 76 disposed within the tissue ablation member lumen 72 of the flexible member 66 to minimize or prevent kinking of the lumen of the flexible member is during deflection. The resilience member 76 is preferably formed of a helical coil of metal or other material that maintains longitudinal flexibility but resists collapse of the circular cross section during deflection of the deflection mechanism 18.

A tensile member 78, having a distal end 80 and a proximal end 82, preferably has the distal end mechanically coupled to the distal deflection cap 70 and is disposed within the deflection mechanism lumen 74 of the flexible member 66. The distal end of the tensile member 80 may also be attached to the distal deflection cap 70 by a variety of methods other than mechanical coupling, including, but not limited to, the use of welding, soldering, or adhesives. FIG. 4 shows the deflection mechanism 18 in its deflected configuration 84, wherein tension has been applied to the tensile member 78, which thereby imparts a torque on the deflection mechanism, which deflects it.

Figure 6:
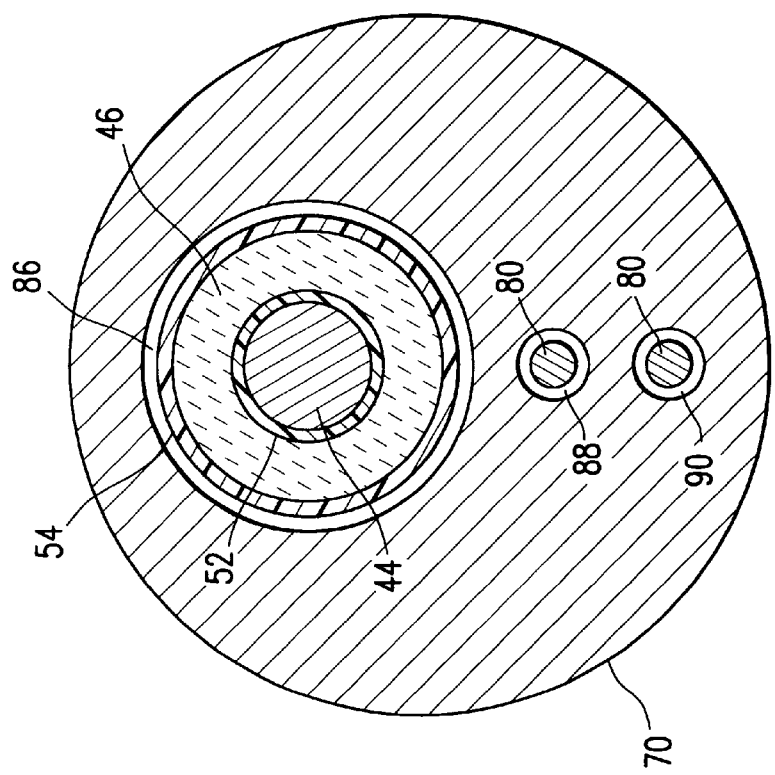
FIG. 6 is a cross sectional view of the elongate probe taken at section 6—6 of FIG. 4.
Figure 5:
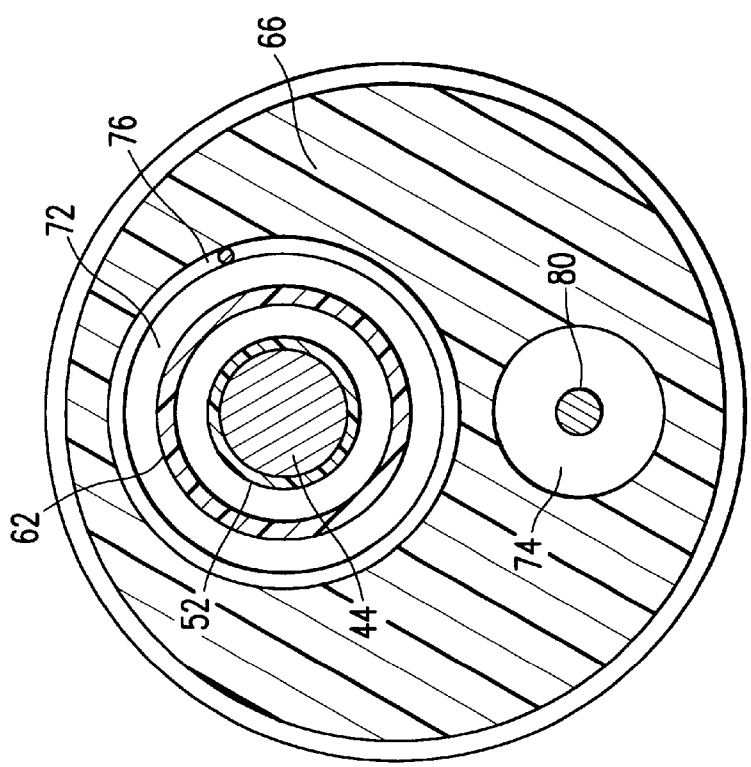
FIG. 5 is a cross sectional view of the elongate probe taken at section 5—5 of FIG. 4.

FIGS. 5 and 6 depict transverse cross sectional views of the deflection mechanism 18 taken as indicated on FIG. 4. In FIG. 5, the optical fiber 44 is coated with protective coating 52 which is disposed within the protective sleeve 62 which is disposed within the tissue ablation member lumen 72 of the flexible member 66. The resilience member 76 is disposed within the tissue ablation member lumen 72 of the flexible member 66 and around the protective sleeve 62 with sufficient spacing to allow the protective sleeve to slide freely therein. The distal end of the tensile member 80 is slidably disposed within the deflection mechanism lumen 74 of the flexible member 66.

In FIG. 6, the lens member 46, sleeve 54, and optical fiber 44 with protective coating 52 are at least partially disposed within a tissue ablation member exit lumen 86 of the distal deflection cap 70. The distal end of the tensile member 80 is preferably disposed within a first retention lumen 88 and a second retention lumen 90 of the distal deflection cap 70.

Figure 7:
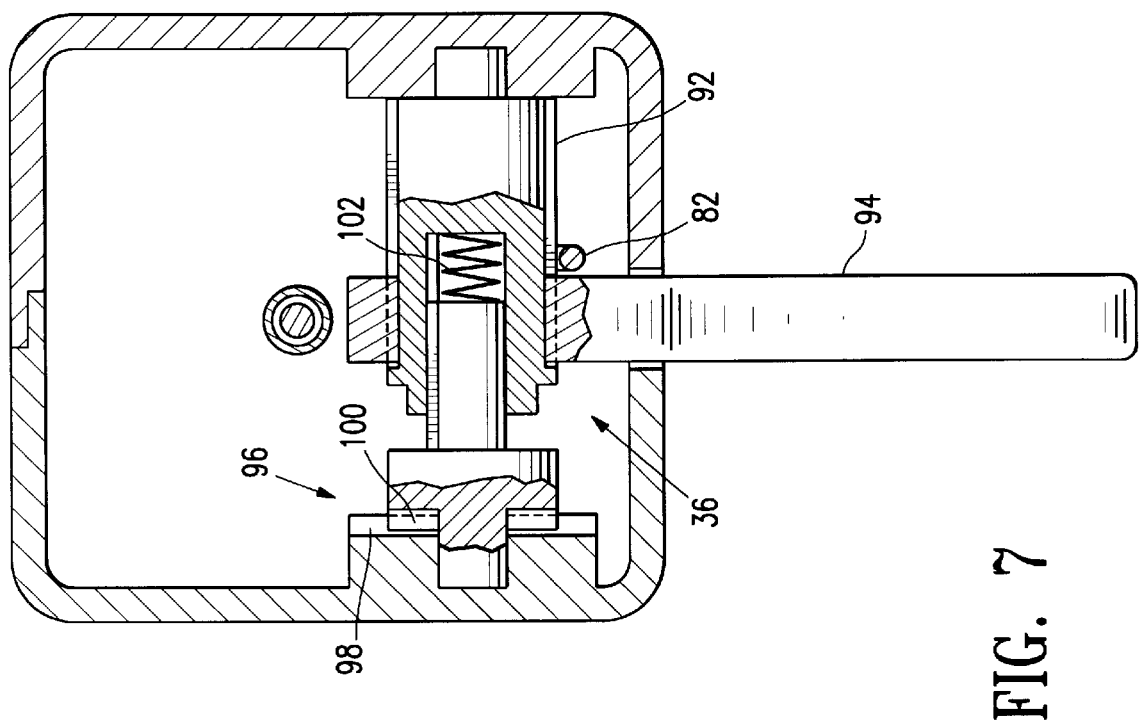
FIG. 7 is a cross sectional view of the handpiece taken at section 7—7 of FIG. 3.

Referring to FIG. 7, the proximal end of the tensile member 82 is attached to a take-up member 92 of the deflection actuator 36. The deflection actuator 36 also comprises a lever member 94 which is mechanically attached to and rotates the take-up member 92, thereby pulling on the proximal end of the tensile member 82. FIG. 4 shows the deflection mechanism 18 in the deflected configuration 84 wherein the lever member 94 as shown in FIG. 7 has been displaced proximally, putting tension on the tensile member 78 which applies a torque to deflection mechanism 18, thereby deflecting the distal end of the elongate probe 14.

Figure 8:
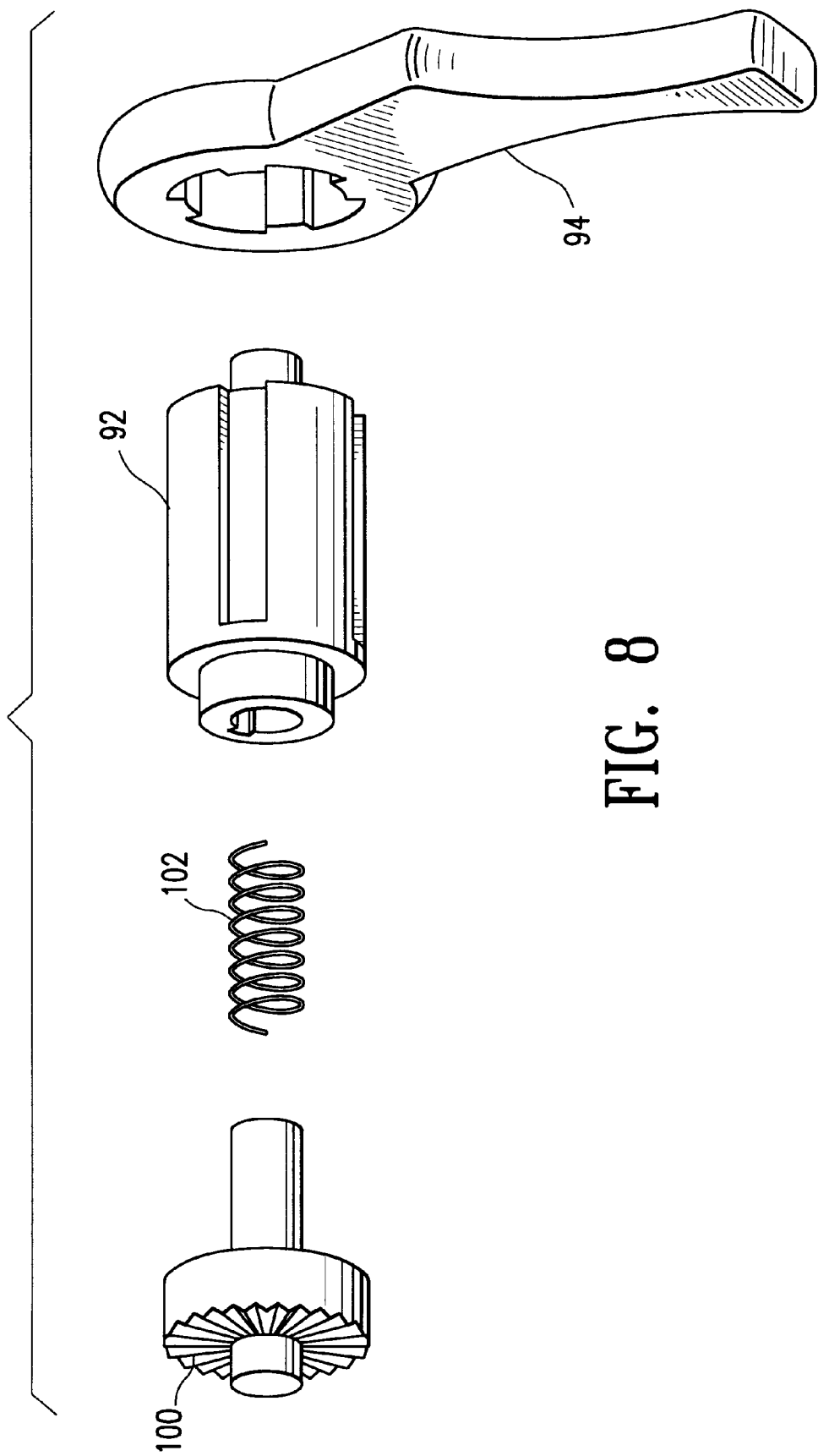
FIG. 8 is an exploded view of a portion of the deflection actuator.

The deflection actuator 36 preferably includes a clutch 96 which is shown in the cross sectional view of FIG. 7 and the exploded view of FIG. 8. The clutch 96 has a handpiece gear 98, an actuator gear 100, a clutch spring 102, and the take-up member 92. The actuator gear 100 is slidably disposed within the take-up member 92 and is forced against the handpiece gear 98 by the clutch spring 102, which is disposed between the actuator gear 100 and the take-up member 92. Movement of the take-up member 92, as restricted by the clutch 96, is such that the lever member 96 can be displaced to cause deflection of the deflection mechanism 18 and left in place to maintain the tension on the proximal end of the tensile member 82, and thus, maintain the deflection of the deflection mechanism and distal end of the elongate probe 14.

Figure 9:
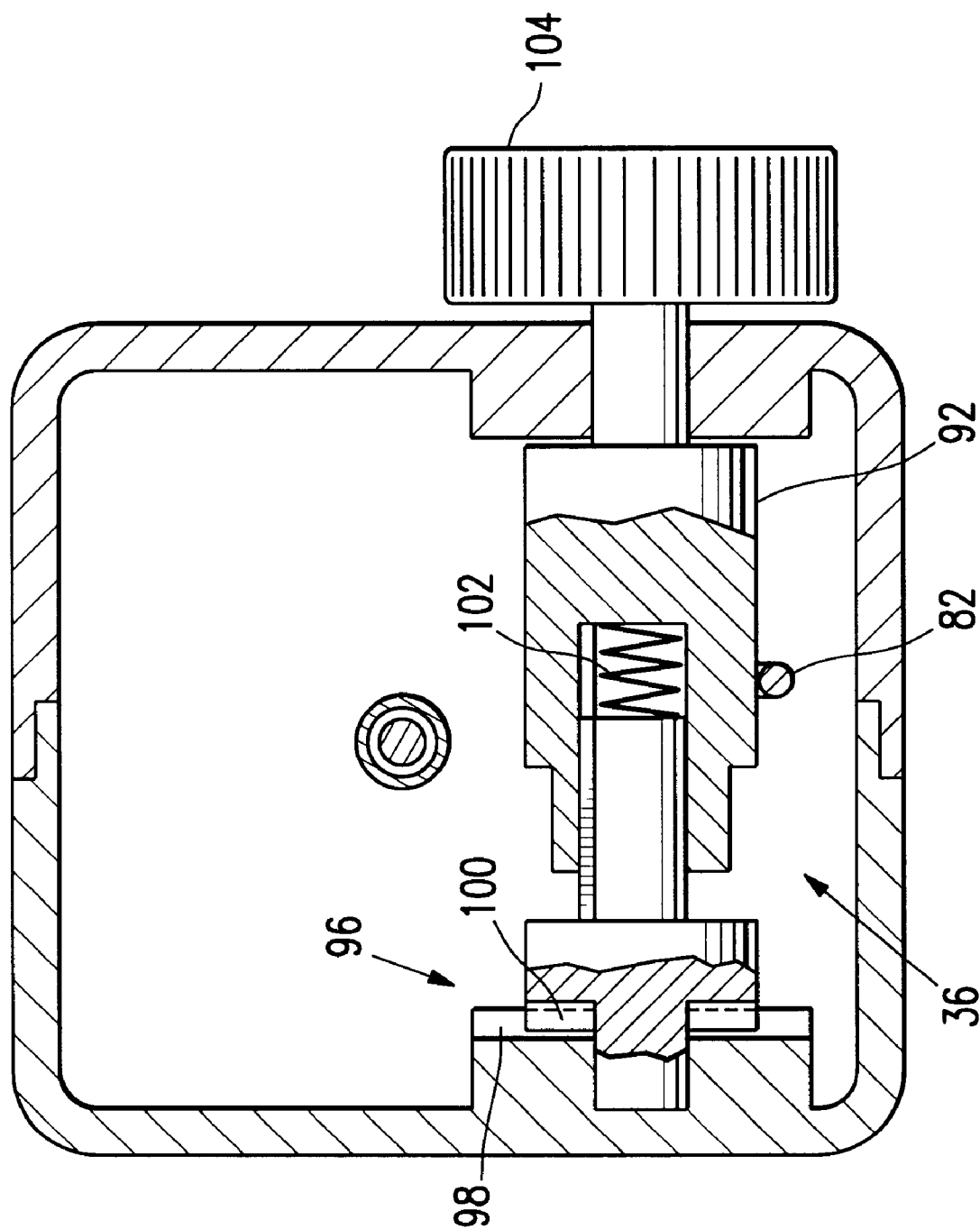
FIG. 9 is a cross sectional view of the handpiece similar to FIG. 7, but showing a thumbwheel in place of the lever member.

An alternative to the lever member 94 component of the deflection actuator 36 is a thumbwheel 104 as depicted in FIG. 9, which is mechanically coupled to the take-up member 92 so that rotation of the thumbwheel imparts rotation to the take-up member. An alternative to applying tension to the proximal end of the tensile member 82 with the deflection actuator 36 is to fix the proximal end of the tensile member and displace the elongate probe 12 in a distal direction relative to the tensile member. This has the same effect of applying tension on the proximal end of the tensile member 82, thereby deflecting it. In other words, deflection of the deflection mechanism 18 is carried out by pushing on the elongate probe 12 rather than pulling on the proximal end of the tensile member 82.

Figure 11:
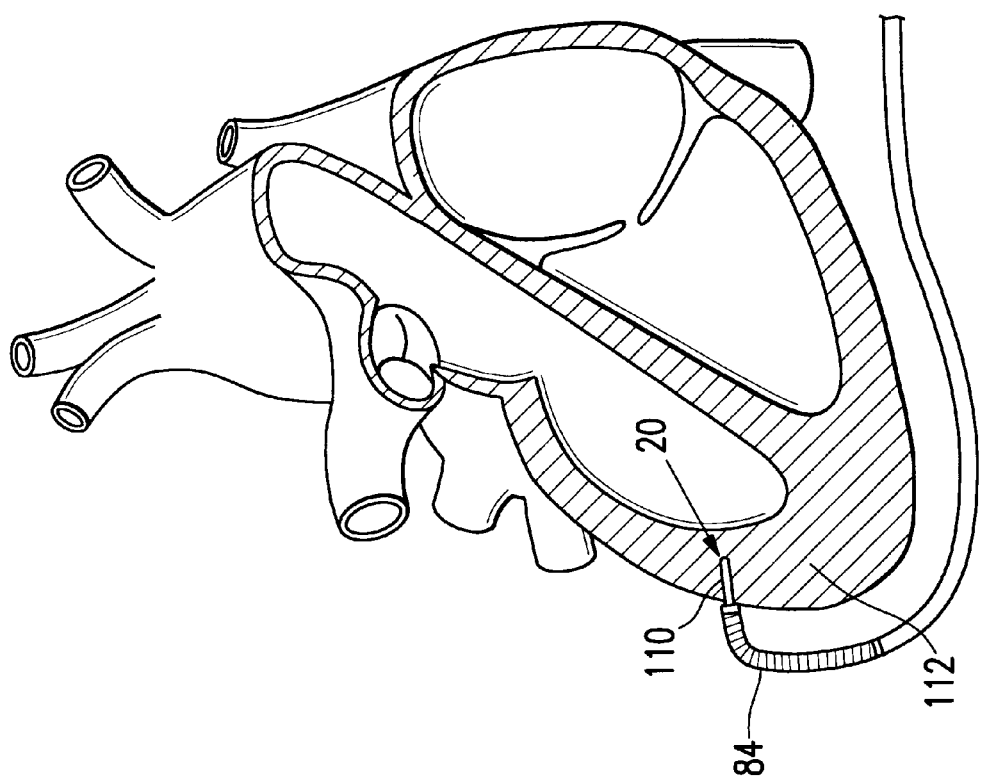
FIG. 11 is a schematic view of the elongate probe in position within a patient's chest during ablation of heart tissue on the posterior side of the heart.
Figure 10:
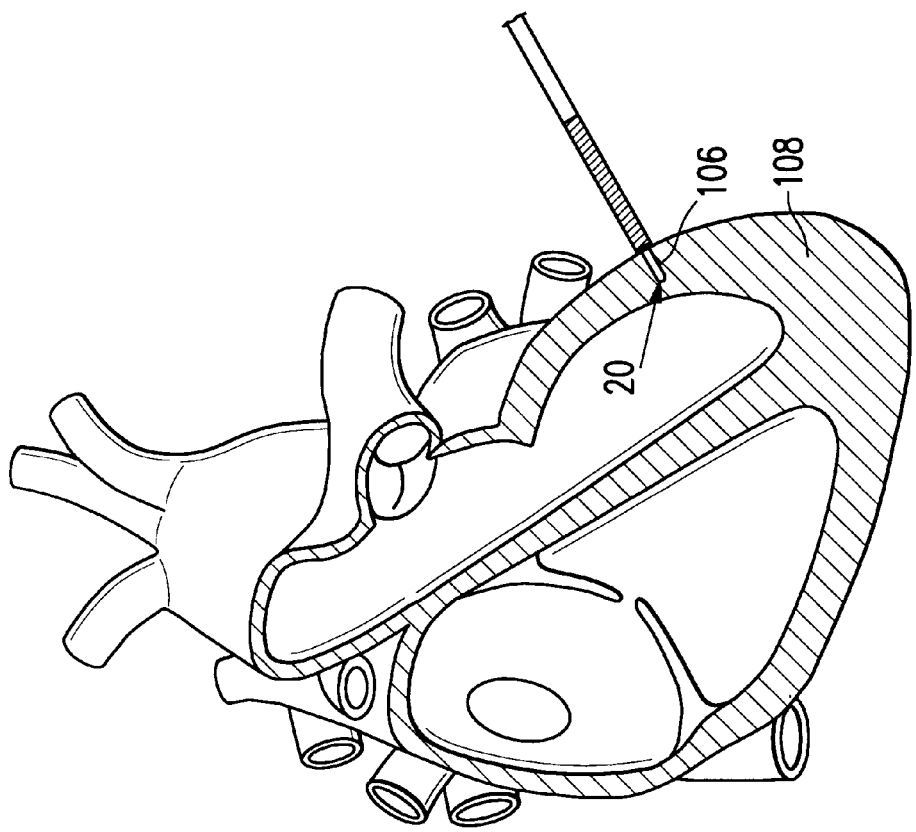
FIG. 10 is a schematic view of the elongate probe in position within a patient's chest during ablation of heart tissue on the front side of the heart.

FIG. 10 and FIG. 11 are diagrammatic views illustrating the use of a preferred embodiment of the invention. FIG. 10 depicts the tissue ablation member 20 forming a channel 106 in the wall of a patient's ventricle 108 with a straight short elongate probe configuration as depicted in FIG. 2A. FIG. 11 depicts the tissue ablation member 20 forming a channel 110 in the wall of a patient's ventricle 112 with an "S" shaped short elongate probe configuration as depicted in FIG. 2C. FIG. 11 also depicts the distal end of the shaped elongate probe 14 in a deflected configuration 84.

Figure 12:
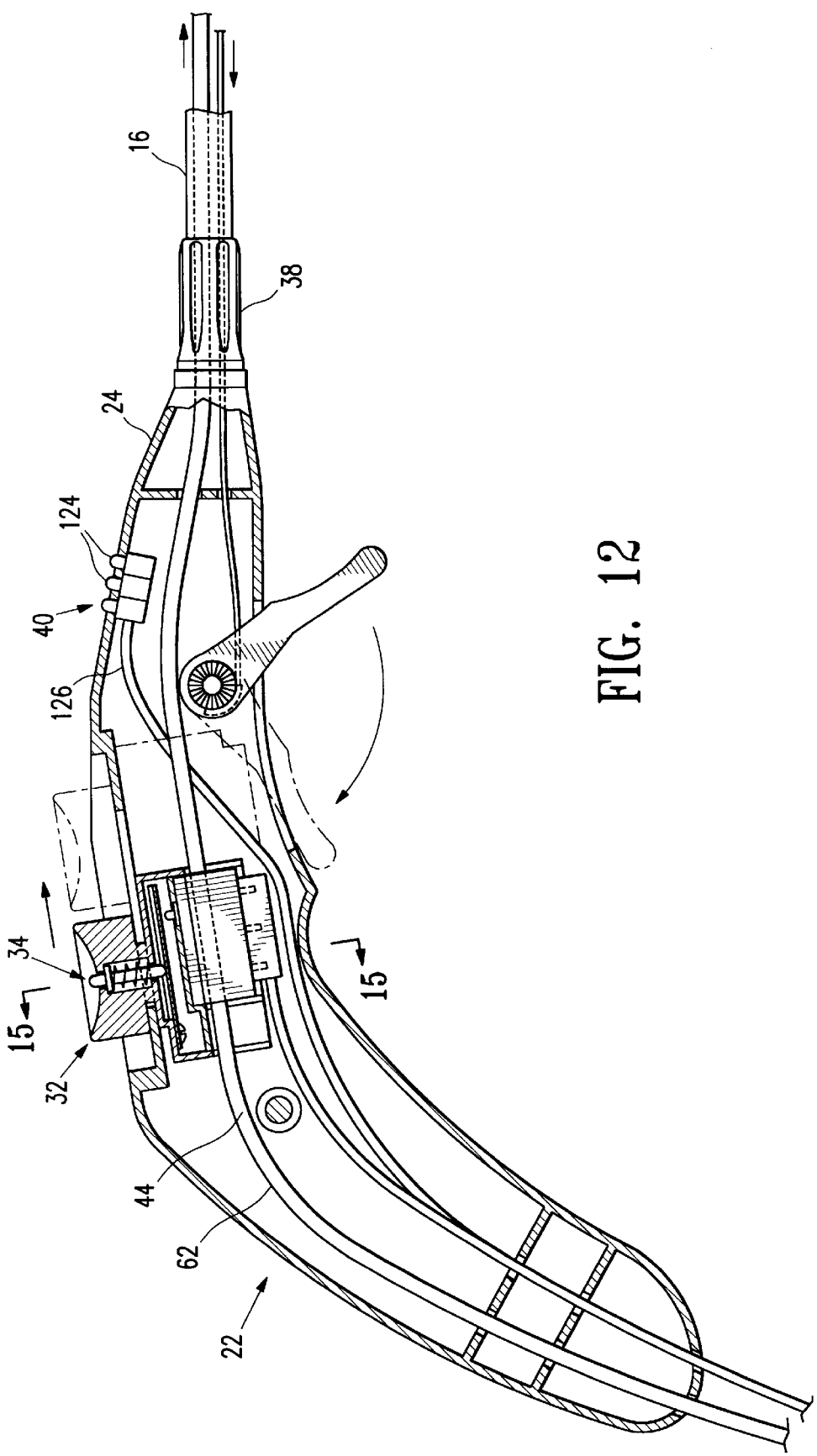
FIG. 12 is an elevational view of the handpiece in partial section.

Referring to FIG. 12, the handpiece 22 is preferably manufactured from molded plastic material, but could also be constructed of any suitable material, such as stainless steel or carbon fiber composite material. The handpiece can be about 4 inches (10.2 cm) to about 12 inches (30.5 cm) in length, preferably about 6 inches (15.3 cm) to about 10 inches (25.4 cm) in length.

Figure 13:
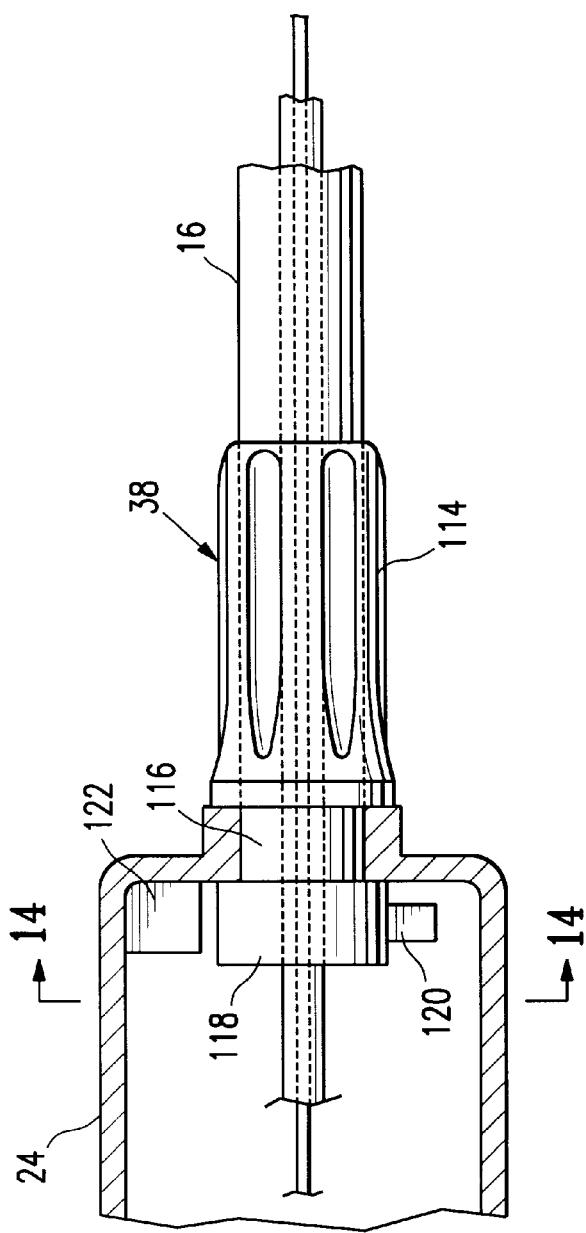
FIG. 13 is a cross sectional view of the distal end of the handpiece and rotator.
Figure 14:
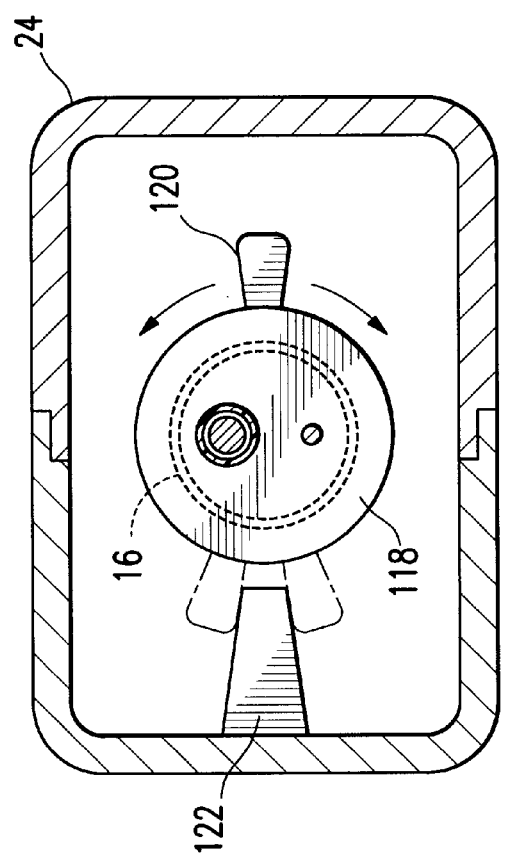
FIG. 14 is a cross sectional view of the distal end of the handpiece taken at 14—14 of FIG. 13.

The proximal end of the elongate shaft 16 is mechanically attached to the distal end of the handpiece 24, or preferably, to a rotator 38 which is rotatably housed within the distal end of the handpiece 24, as shown in more detail in FIG. 13 and FIG. 14. This allows the elongate probe 12 to be rotated and manipulated within the patient while the handpiece 22 is outside the patient. As shown in FIG. 13 and FIG. 14, the rotator 38 comprises a knurled portion 114, a shaft portion 116 and a flange 118. The flange 118 has a stop peg 120 mechanically attached to it and operatively configured to mechanically engage a rotator stop 122 which is attached to the distal end of the handpiece 24. This configuration allows the elongate probe 12 to be rotated about its longitudinal axis, limited to about 360 degrees of rotation or less.

Referring again to FIG. 12, the hand piece 22 may also comprise an indicator 40 disposed on the hand piece 22 which typically comprises a plurality of light-emitting diodes 124 electrically coupled to the ablation energy source 42 by an electric cable 126 to indicate the status of the ablation energy source, i.e. whether it is ready, or in standby mode. The indicator may also be comprised of a plurality of incandescent lights or the like. The indicator 40 would also be useful for alternative ablation energy sources used to power the tissue removal member 20 at the distal end of the elongate probe 14, such as radio frequency, ultrasonic, high-pressure water jet, abrasive rotational or other energy types for tissue ablation or non-ablative tissue treatment.

Preferably, the advancement mechanism 32, as depicted in FIG. 12, is slidably mounted on the handpiece 22 and is mechanically coupled to the optical fiber 44 and protective sleeve 62 such that the advancement mechanism 32 can be used to axially translate the fiber optic 44 and tissue ablation member 20 in relation to the elongate probe 12.

An activation mechanism 34 is preferably housed within the advancement mechanism 32 and is configured to control activation of the tissue ablation member 20. In addition, the activation mechanism 34 is housed within and coupled to the advancement mechanism 32 in such a manner that the operator can simultaneously activate and advance the tissue ablation member 20 from the handpiece 22 with one finger or thumb, thereby facilitating a coordination of functions.

Figure 15:
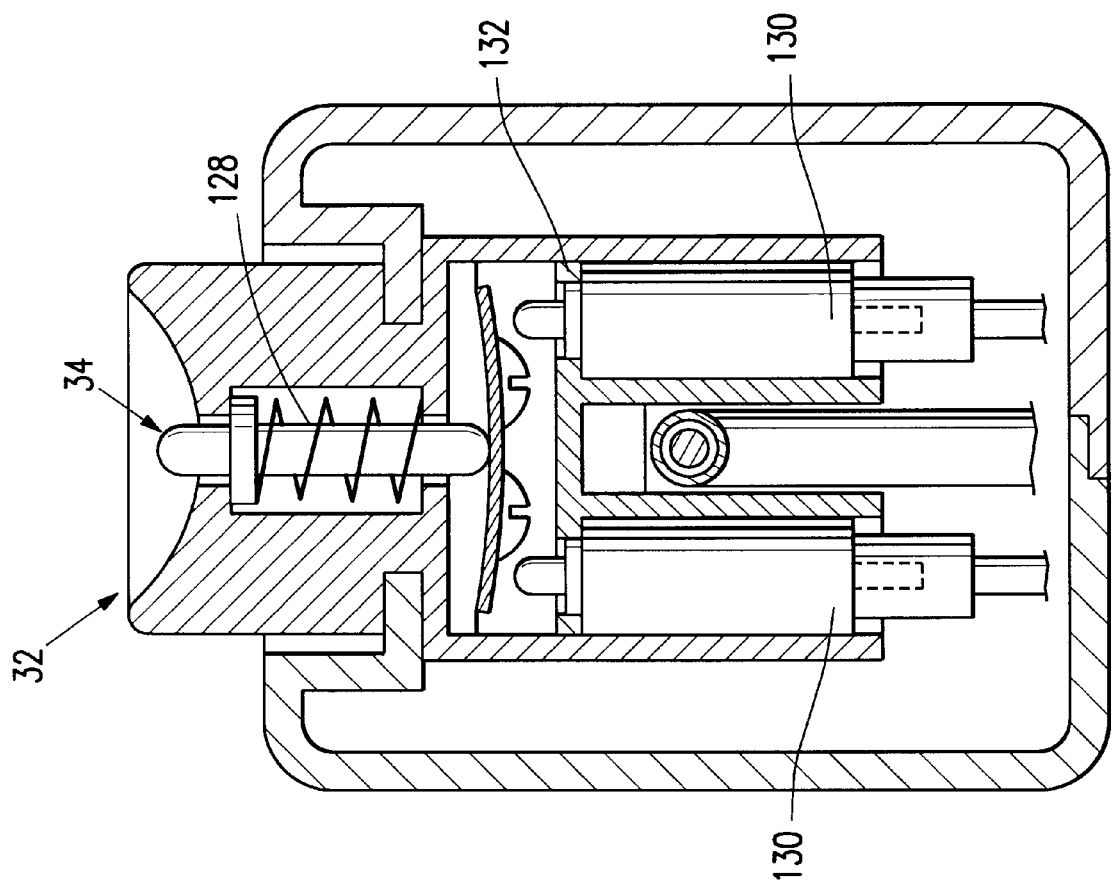
FIG. 15 is a cross sectional view of the handpiece taken at section 15—15 of FIG. 12.

Referring to FIG. 15, the activation mechanism 34 comprises a button shaft 128 housed within the advancement mechanism 32. The button shaft 128 and advancement mechanism 32 are configured so that an operator's thumb can depress the button shaft, which activates the tissue ablation member 20, and axially translate the advancement mechanism 32, simultaneously. The activation mechanism 34 preferably further comprises a plurality of electrical switches 130, which are held in place by a mounting bracket 132 and which are configured to function simultaneously.

Figure 17:
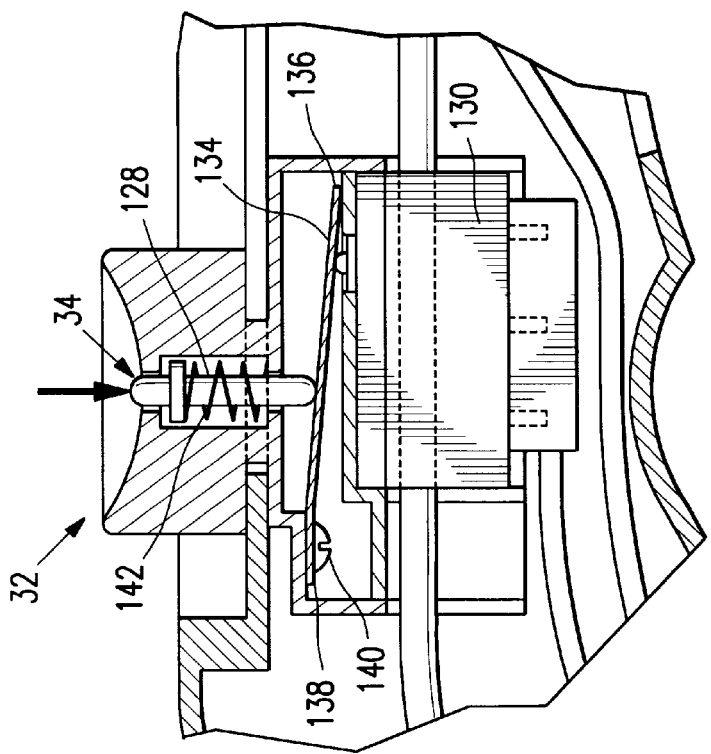
FIG. 17 is a magnified view of the advancement mechanism and actuation mechanism shown with the button shaft depressed.
Figure 16:
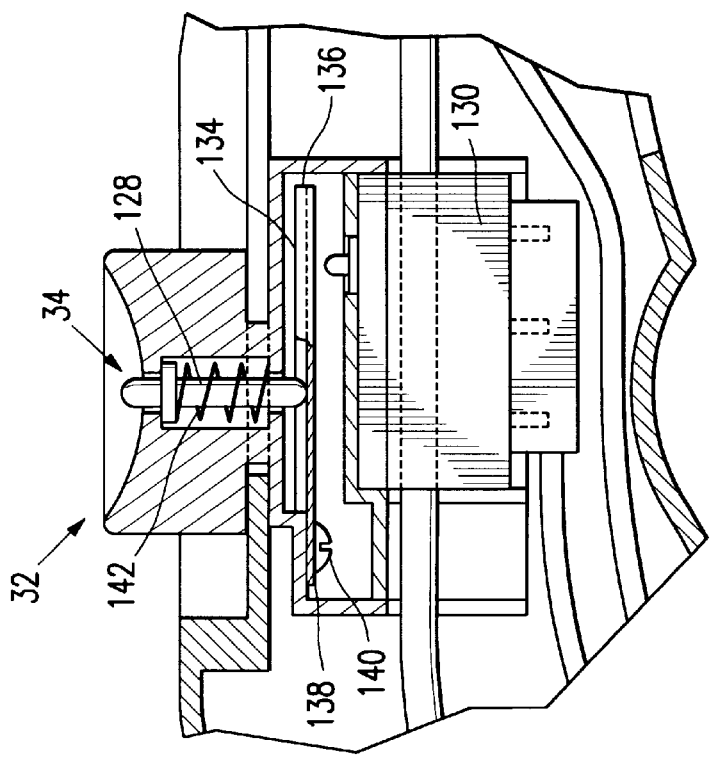
FIG. 16 is a magnified view of the advancement mechanism and actuation mechanism.

Referring to FIG. 16 and FIG. 17, the embodiment of the activation mechanism 34 also preferably comprises a cantilever beam 134 which has a free end 136 and a fixed end 138 which is attached to the advancement mechanism 32 with fasteners 140. The cantilever beam 134 is mechanically coupled to the button shaft 128, and is configured in a spaced relation to the electrical switches 130, such that depression of the button shaft 128 translates the cantilever beam 134 which engages the electrical switches 130 substantially simultaneously, as shown in FIG. 17. The cantilever beam 134 provides restoring force to button shaft 128 in addition to a restoring force provided by a button shaft spring 142, returning it to its initial position when the operator's finger is removed from the activation mechanism 34.

The cantilevered beam 134 provides substantially simultaneous activation of switches 130 by resisting displacement as force is applied to it by button shaft 128, until a threshold force is reached, at which point the cantilever beam collapses suddenly with a resulting high acceleration of the free end 136. The high acceleration of the free end 136 of the cantilevered beam 134 results in a high velocity at the time of engagement of the electrical switches 130, thus activating the electrical switches substantially simultaneously.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A surgical tissue ablation device comprising:
   a) an elongate probe having a proximal end and a distal end;
   b) at least one tissue ablation member at the distal end of the elongate probe;
   c) an activation mechanism which is energetically coupled to the at least one tissue ablation member and which is slidably attached at the proximal end of the elongate probe for activating the at least one tissue ablation member;
   d) an advancement mechanism which is slidably attached to the elongate probe and coupled to the at least one tissue ablation member for advancing the at least one tissue ablation member and which is operatively coupled to the activation mechanism to facilitate simultaneous operation of both with manual contact at a single site; and e) a shaping device coupled to the elongate probe to facilitate at least one curve of the elongate probe.

2. The device of claim 1 wherein the shaping device is comprised of a deflection mechanism at the distal end of the elongate probe and a deflection actuator located at the proximal end of the probe, the deflection mechanism being mechanically coupled to the deflection actuator, operation of the deflection actuator results in the deflection of the distal end of the elongate probe.

3. The device of claim 2 wherein the shaping device further comprises a tensile member having a proximal end and a distal end, the distal end of the tensile member being attached to the distal end of the elongate probe offset from the longitudinal axis of the probe.

4. The device of claim 3 wherein the proximal end of the tensile member is attached to the deflection actuator which is configured to apply tension to the tensile member such that tension on the tensile member imparts a torque on the distal tip of the elongate probe resulting in deflection of the distal end of the probe.

5. The device of claim 3 wherein the distal end of the tensile member is mechanically attached to the distal end of the elongate probe.

6. A surgical tissue ablation device comprising:
a) an elongate probe having a proximal end and a distal end;
b) at least one tissue ablation member at the distal end of the elongate probe;
c) a handpiece which has an interior cavity and which has a distal end and a proximal end with the distal end of the handpiece secured to the proximal end of the elongate probe;
d) an activation mechanism which is attached to the handpiece and which is energetically coupled to the at least one tissue ablation member for activating the at least one tissue ablation member;
e) an advancement mechanism which is slidably mounted to the handpiece and mechanically coupled to the at least one tissue ablation member for advancing the at least one tissue ablation member as tissue is ablated with said activation mechanism and advancement mechanism operatively coupled to each other to facilitate simultaneous operation of both mechanisms with manual contact at a single site; and
f) a shaping device coupled to the elongate probe to facilitate at least one curve of the elongate probe.

7. The device of claim 6 wherein the handpiece further comprises a rotator disposed upon the front end of the handpiece mechanically coupled to the proximal end of the elongate probe for rotating the elongate probe about its longitudinal axis.

8. The device of claim 7 further comprising a rotator stop which limits the rotator to less than 360 degrees of rotation.

9. The device of claim 6 wherein the shaping device comprises a deflection mechanism at its distal end and the handpiece further comprises a deflection actuator disposed thereon which is operatively coupled to the deflection mechanism such that activation of the deflection actuator causes the deflection mechanism to deflect the distal end of the elongate probe.

10. The device of claim 9 wherein the deflection mechanism is comprised of:
a flexible member at the distal end of the elongate probe with at least one lumen extending therethrough; and
a tensile member having a proximal end and a distal end, with the distal end attached to the elongate probe distally of the flexible member and offset from the longitudinal axis of the probe, and wherein the deflection actuator is comprised of a take-up member disposed within the interior cavity of the handpiece which has a slot to capture the proximal end of the tensile member and a lever member attached to the take-up member that extends outside the outer wall of the handpiece so that it can be activated by an operator of the device who deflects the lever which causes movement of the take-up member, thereby imparting tension on the tensile member and deflection of the distal end of the elongate probe.

11. The device of claim 10 wherein the deflection actuator is comprised of a take-up member disposed within the outer wall of the handpiece, said take-up member having a slot to capture the proximal end of the tensile member, and a thumbwheel member attached to the take-up member that extends outside the outer wall of the handpiece so that it can be activated by an operator of the device who rotates the thumbwheel which causes movement of the take-up member, thereby pulling on the tensile member which is attached thereto.

12. The device of claim 10 wherein the deflection actuator is comprised of an extendible shaft member coupled to the proximal end of the elongate probe and slidably disposed within the distal end of the handpiece with the proximal end of the tensile member affixed to the handpiece whereby the extendible shaft is displaced distally which in turn displaces the elongate probe distally which puts tension on the tensile member which then deflects the distal end of the elongate probe.

13. The device of claim 10 wherein the deflection actuator further comprises a clutch which is mechanically coupled to the take-up member and prevents movement of the take-up member such that the take-up member will remain stationary in the absence of operator applied force and allows fixation of distal end deflection.

14. The device of claim 10 wherein the at least one tissue ablation member is comprised of a lens member coupled by an optical fiber to a laser energy source.

15. The device of claim 14 wherein the optical fiber is disposed within the elongate probe and the elongate probe further comprises at least one resilience member disposed about the optical fiber which prevents compression and mechanical distortion of the optical fiber during deflection of the distal end of the elongate probe.

16. The device of claim 15 wherein the at least one resilience member is comprised of a coiled wire disposed about the distal end of the elongate probe.

17. The device of claim 14 wherein the lens member is mechanically crimped to the optical fiber.

18. The device of claim 6 wherein the handpiece further comprises at least one indicator which is disposed upon the handpiece and which indicates the status of the at least one tissue ablation member.

19. The device of claim 18 wherein the at least one indicator is comprised of at least one light emitting diode.

20. The device of claim 6 wherein the activation mechanism is comprised of at least one electrical switch which is electrically coupled to the at least one tissue ablation member.

21. The device of claim 20 wherein the activation mechanism further comprises an enclosure surrounding the at least one electrical switch, the enclosure being sealed to prevent the ingress of moisture.

22. The device of claim 6 wherein the activation mechanism is comprised of a plurality of electrical switches in spaced relation to a cantilever beam such that the switches are activated substantially simultaneously by the cantilever beam.

23. The device of claim 22 wherein the activation mechanism further comprises a button shaft, the cantilever beam being mechanically coupled to the button shaft.

24. The device of claim 23 wherein the cantilever beam supports increasing force applied to it from the button shaft until a threshold force is reached at which time the cantilever beam will fail resulting in rapid displacement of the cantilever beam which is then directed to the plurality of electrical switches in order to activate them substantially simultaneously.

25. The device of claim 6 wherein the at least one tissue ablation member is comprised of a radio frequency ablation probe.

26. The device of claim 6 wherein the at least one tissue ablation member is comprised of an ultrasonic ablation probe.

27. The device of claim 6 wherein the at least one tissue ablation member is comprised of a high pressure water jet ablation probe.

28. The device of claim 6 wherein the at least one tissue ablation member is comprised of a rotating mechanical tissue ablation probe.

29. A surgical tissue ablation device comprising:
 a) an elongate probe having a proximal and a distal end, a deflection mechanism disposed at the distal end which is comprised of a flexible member with at least one lumen extending therethrough and a tensile member disposed within the lumen which has a proximal end and a distal end and is affixed to the distal end offset from the longitudinal axis of the elongate probe;
 b) a tissue ablation member at the distal end of the elongate probe;
 c) a handpiece which has an inner chamber, a proximal end and a distal end with the distal end of the hand piece attached to the proximal end of the elongate probe;
 d) an advancement mechanism which is slidably mounted on the handpiece and which is mechanically coupled to a portion of the tissue ablation member disposed within a chamber within the handpiece for axially translating the tissue ablation member;
 e) an activation mechanism housed in the handpiece which is energetically coupled to the tissue ablation member and which energetically controls activation of the tissue ablation member;
 f) a deflection actuator which is housed in the handpiece and comprises a take-up member disposed within the interior cavity of the handpiece and having a slot to capture the proximal end of the tensile member and a lever member attached to the take-up member that extends outside the outside wall of the handpiece so that it can be activated by an operator of the device who deflects the lever which causes rotation of the take-up member, thereby imparting tension on the tensile member; and
 g) a rotator which is rotatably housed in the distal end of the handpiece and attached to the proximal end of the elongate probe and which rotates the elongate probe about its axis.

30. The device of claim 29 wherein the activation mechanism and advancement mechanism are operatively coupled such that both can be operated simultaneously with one finger or thumb.

31. The device of claim 29 further comprising an indicator disposed on the handpiece which indicates the status of the tissue ablation member.

32. A surgical tissue ablation device comprising:
 a) an elongate probe having a proximal end and a distal end;
 b) at least one tissue ablation member at the distal end of the elongate probe;
 c) an activation mechanism which is energetically coupled to the at least one tissue ablation member and which is disposed at the proximal end of the elongate probe for activating the at least one tissue ablation member;
 d) an advancement mechanism which is disposed at the proximal end of the elongate probe and coupled to the at least one tissue ablation member for advancing the at least one tissue ablation member and which is operatively coupled to the activation mechanism to facilitate simultaneous operation cf both the activation mechanism and advancement mechanism with manual contact at a single site; and
 e) a shaping device coupled to the elongate probe to facilitate at least one curve of the elongate probe.

33. A surgical tissue ablation device comprising:
 a) an elongate probe having a proximal end and a distal end;
 b) at least one tissue ablation member at the distal end of the elongate probe;
 c) a handpiece which has an interior cavity and which has a distal end and a proximal end with the distal end of the handpiece secured to the proximal end of the elongate probe;
 d) an activation mechanism which is disposed at the proximal end of the elongate probe and which is energetically coupled to the at least one tissue ablation member for activating the at least one tissue ablation member;
 e) an advancement mechanism which is disposed at the proximal end of the elongate probe and mechanically coupled to the at least one tissue ablation member for advancing the at least one tissue ablation member as tissue is ablated with said activation mechanism and advancement mechanism operatively coupled to each other to facilitate simultaneous operation of both mechanisms with manual contact at a single site; and
 f) a shaping device coupled to the elongate probe to facilitate at least one curve of the elongate probe.

34. A surgical tissue ablation device comprising:
 a) an elongate probe having a proximal and a distal end, a deflection mechanism disposed at the distal end which is comprised of a flexible member with at least one lumen extending therethrough and a tensile member disposed within the lumen which has a proximal end and a distal end and is affixed to the distal end offset from the longitudinal axis of the elongate probe:
 b) a tissue ablation member at the distal end of the elongate probe;
 c) a handpiece which has an inner chamber, a proximal end and a distal end with the distal end of the hand piece attached to the proximal end of the elongate probe;
 d) an advancement mechanism which is disposed at the proximal end of the elongate probe which is mechanically coupled to a portion of the tissue ablation member for axially translating the tissue ablation member;

e) an activation mechanism which is disposed at the proximal end of the elongate probe and which is energetically coupled to the tissue ablation member and which energetically controls activation of the tissue ablation member;

f) a deflection actuator which is housed in the handpiece and comprises, a take-up member disposed within the interior cavity of the handpiece and having a slot to capture the proximal end of the tensile member and a lever member attached to the take-up member that extends outside the outside wall of the handpiece so that it can be activated by an operator of the device who deflects the lever which causes rotation of the take-up member, thereby imparting tension on the tensile member; and g) a rotator which is rotatably housed in the distal end of the handpiece and attached to the proximal end of the elongate probe and which rotates the elongate probe about its axis.

* * * * *